(12) United States Patent
Siew-Wah et al.

(10) Patent No.: US 8,226,745 B2
(45) Date of Patent: Jul. 24, 2012

(54) MINIATURE OXYGEN CONCENTRATORS AND METHODS

(75) Inventors: Chai Siew-Wah, Bethlehem, PA (US); Shivaji Sircar, Allentown, PA (US); Mayuresh V. Kothare, Bethlehem, PA (US)

(73) Assignee: Lehigh University, Bethlehem, PA (US)

( * ) Notice: Subject to any disclaimer, the term of this patent is extended or adjusted under 35 U.S.C. 154(b) by 323 days.

(21) Appl. No.: 12/769,283

(22) Filed: Apr. 28, 2010

(65) Prior Publication Data
US 2010/0300285 A1    Dec. 2, 2010

Related U.S. Application Data

(60) Provisional application No. 61/173,352, filed on Apr. 28, 2009.

(51) Int. Cl.
*B01D 53/047* (2006.01)

(52) U.S. Cl. .................. 95/98; 95/130; 96/132

(58) Field of Classification Search .............. 95/96–98, 95/104, 105, 117, 130; 96/121, 132, 143, 96/144; 128/204.18
See application file for complete search history.

(56) References Cited

U.S. PATENT DOCUMENTS

| | | | |
|---|---|---|---|
| 4,756,723 A | 7/1988 | Sircar | |
| 4,959,083 A | 9/1990 | Garrett | |
| 4,964,888 A * | 10/1990 | Miller | 95/95 |
| 5,071,449 A | 12/1991 | Sircar | |
| 5,074,892 A * | 12/1991 | Leavitt | 95/96 |
| 5,674,311 A | 10/1997 | Notaro et al. | |
| 5,827,358 A | 10/1998 | Kulish et al. | |
| 6,506,234 B1 * | 1/2003 | Ackley et al. | 95/96 |
| 6,551,384 B1 | 4/2003 | Ackley et al. | |
| 6,723,155 B2 * | 4/2004 | Weyrich et al. | 95/120 |
| 7,121,276 B2 | 10/2006 | Jagger et al. | |
| 7,541,007 B2 | 6/2009 | Pattekar et al. | |
| 2002/0014159 A1 * | 2/2002 | Tatsumi et al. | 96/130 |
| 2003/0056649 A1 * | 3/2003 | Lee et al. | 95/90 |
| 2008/0134889 A1 * | 6/2008 | Zhong et al. | 95/148 |

FOREIGN PATENT DOCUMENTS
WO    WO 2006/044172 A2    4/2006

* cited by examiner

*Primary Examiner* — Frank Lawrence, Jr.
(74) *Attorney, Agent, or Firm* — Rhoads & Sinon LLP; Kurt L. Ehresman (57) ABSTRACT

Provided herein are new compact and miniature oxygen concentrator apparatus, as well as methods incorporating use of the apparatus. The apparatus and methods utilize selected cycle times, adsorbent specifications and novel conditions to produce a fast Pressure Swing Adsorption ("PSA") system. The oxygen concentrator apparatus and methods herein have significant utility in the fields of biotechnology, engineering, and medicine. A particularly advantageous use of this invention is as a "snap on" portable oxygen concentrator, where piped compressed air is already available such as in civil and military hospitals, ambulances, air craft cabins, mobile fish tanks, etc. Those embodiments eliminate the need for dedicated moving machinery (blower, compressor, vacuum pump) normally associated with a conventional PSA oxygen concentrator.

19 Claims, 9 Drawing Sheets

Schematic Flow Diagram for Snap-On & Stand-alone Medical O2 Generator

Schematic Flow Diagram for Snap-On & Stand-alone Medical O2 Generator

Figure 9

MINIATURE OXYGEN CONCENTRATORS AND METHODS

CROSS-REFERENCE TO RELATED APPLICATIONS

This application claims the priority of U.S. 61/173,352, filed on Apr. 28, 2009, the entire contents of which are incorporated herein reference.

FIELD

This application describes a rapid cycle pressure swing adsorption (PSA) oxygen concentrator apparatus and related methods for operating the apparatus utilizing a range of preferred cycle times, which was not previously identified, in conjunction with selected adsorbents of preferred specifications. The oxygen concentrator apparatus and methods herein have significant utility in the fields of biotechnology, engineering, and medicine. A particularly advantageous use of this invention is as a "snap on" portable oxygen concentrator where piped compressed air is available such as in civil and military hospitals, ambulances, air craft cabins, mobile fish tanks, etc., thus eliminating the need for a dedicated moving machine (blower, compressor, vacuum pump) normally associated with a conventional PSA oxygen concentrator.

BACKGROUND

Oxygen is commonly administered to living organisms, and in particular, humans, for medical and survival purposes. For example, a significant population of humans require administration of supplemental oxygen to alleviate respiratory disorders, such as COPD. Such supplemental oxygen is traditionally supplied by compressed or liquid oxygen cylinders. However, more recently, in situ PSA medical oxygen concentrators for individual use have been developed, and are being used in such environments as residential homes and during travel for mobile applications.

Some examples of known concentrators are described in: U.S. Pat. No. 7,121,276 B2 to Jagger et al. (2006) for "Personal Oxygen Concentrator"; U.S. Pat. No. 6,551,384 B1 to Ackley and Zhong (2003) for "Medical Oxygen Concentrator"; and U.S. Pat. No. 5,827,358 to Kulish and Swank (1998) for "Rapid Cycle Pressure Swing Adsorption Oxygen Concentrator Method and Apparatus"; and International Publication No.: WO 2006/044172 A2 to McCombs et. al. (2006) for "Mini-Portable Oxygen Concentrator."

It has been a longstanding goal of oxygen concentrator designers to reduce adsorber size, while still providing for production of ~2-8 liters/minute of about ~90-93% pure $O_2$ from ambient air for home or hospital medical use. In seeking to accomplish that objective, one could employ any number of mechanisms, for instance, cyclic adsorptive process such as Pressure Swing Adsorption (PSA), Vacuum Swing Adsorption (VSA), or Pressure-Vacuum Swing Adsorption (PVSA), and by employing a $N_2$ selective zeolite adsorbent. Despite the theories and available technology, nonetheless, this long-standing critical goal for the industry remains unmet. As described above, numerous patents have been issued which describe various process designs to approach this goal by manipulating the type of the adsorbent used, the synthesis of the process cycle steps, the total process cycle time, the adsorber and valving design, etc. One popular approach is to reduce the process cycle time so that the adsorbent is used more frequently, thereby increasing its specific $O_2$ productivity rate. Cycle times of few minutes (large commercial oxygen generators) to few seconds (small medical oxygen generators) are generally used. Cycle time of a fraction of a second has also been claimed.

Despite the existence of such oxygen concentrator technology described in the literature, there exists a continuing and unmet need for even smaller, and preferably miniature, efficient, oxygen concentrator apparatus and systems that are suitable for individual use, both in terms of size and performance, as well as in terms of cost. Further, there is a need for miniature oxygen concentrators that can snap on or otherwise be installed on existing compressed air lines to provide a ready source of oxygen without the need for air compressor, air blower and/or vacuum pumps and other heavy components to provide oxygen having a purity of more than about 90%.

SUMMARY

Provided herein are new and inventive apparatus and methods for producing concentrated oxygen. The apparatus and methods allow for unprecedented advantages over known oxygen concentrators, such as reduction in size, weight, maintenance, power consumption, cycle times, and efficiency, among other things.

In one embodiment, methods are provided for an inventive PSA gas separation and oxygen concentrator process. A rapid cyclic pressure swing adsorption (PSA) method for producing an oxygen enriched gaseous product containing more than 85 mole % oxygen. The method comprising the steps of: a) providing a feed gas comprising compressed ambient air; b) providing a gas separation apparatus comprising at least one adsorber column, the adsorber column packed with at least a layer of a desiccant adsorbent comprising particles of more than 1.0 mm hydraulic diameter in the feed gas side and at least a layer of a nitrogen selective particles of less than 0.5 mm hydraulic diameter in the product gas side; and c) carrying out a PSA separation process. The process includes the steps of: (1) co-currently pressurizing the at least one adsorber column using the received compressed ambient air; (2) co-currently directing flow of the compressed ambient air to produce an oxygen enriched product gas at a near feed gas pressure; (3) performing counter-current depressurization of the at least one adsorber column to a near ambient pressure; and (4) performing a counter-current oxygen purge at ambient or sub-ambient pressure using at least a portion of the oxygen enriched product gas.

In another embodiment, apparatus are provided for performing the inventive PSA process. For example, an apparatus for executing rapid cyclic pressure swing adsorption (PSA) methods for producing an oxygen enriched gaseous product containing more than 85 mole % oxygen, the apparatus comprising: a) a gas separation apparatus comprising at least one adsorber column, the adsorber column packed with at least a layer of a desiccant adsorbent comprising articles of more than 1.0 mm hydraulic diameter in the feed gas side and at least a layer of a nitrogen selective particles of less than 0.5 mm hydraulic diameter in the product gas side; and b) means for carrying out a PSA separation process. In this example, the process includes the steps of: (1) co-currently pressurizing the at least one adsorber column using the received compressed ambient air; (2) co-currently directing flow of the compressed ambient air to produce an oxygen enriched product gas at a near feed gas pressure; (3) performing counter-current depressurization of the at least one adsorber column to a near ambient pressure; and (4) performing a counter-current oxygen purge at ambient or sub-ambient pressure using at least a portion of the oxygen enriched product gas Additional features may be understood by referring to the accompanying drawings, which should be read in conjunction with the following detailed description and examples.

DETAILED DESCRIPTION

Provided herein are new and useful compact, portable, efficient apparatus and methods for producing concentrated oxygen.

Figure 1:
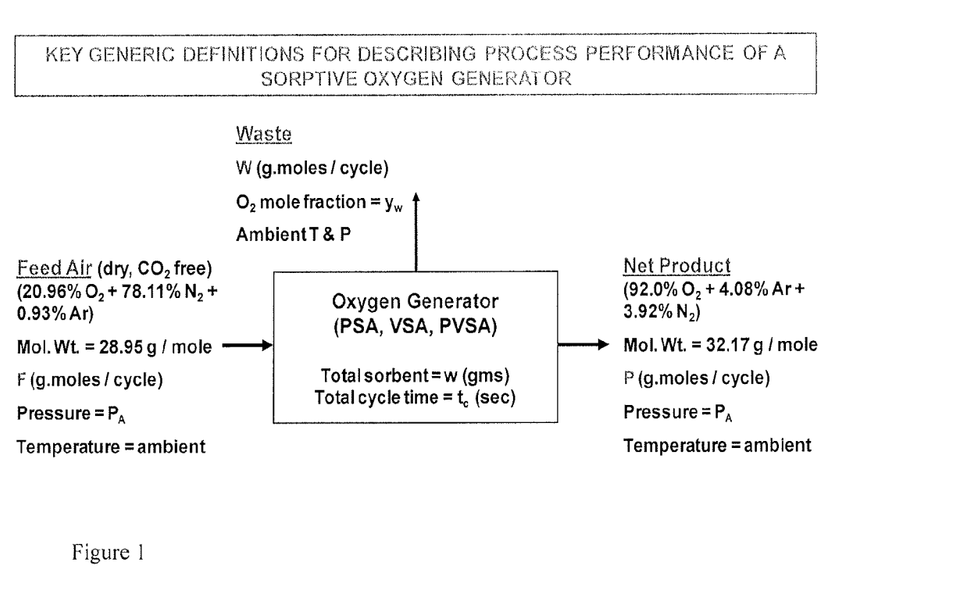
FIG. 1 schematically illustrates the applicable general processes and terminology relating to a sorptive oxygen concentrator as described herein.

It is often customary by the industry to represent the oxygen ($O_2$) production rate from an adsorbent oxygen concentrator (or "sorber") in terms of tons per day of contained $O_2$ ($TPD_c$). For example, the $TPD_c$ rate for the schematic system shown in FIG. 1 hereof is given by 2.816 P/$t_c$. FIG. 1 is a schematic box diagram for a generic sorptive oxygen generator system which can be a PSA, VSA, or PVSA process consisting of one or more parallel sorbers. The streams entering and leaving the system (containing a total of w gms of the sorbent) are the air feed (F), product $O_2$ (P), and the waste gas (W). The variables F, P and W are specific amounts (g·moles/cycle). The total cycle time for the process is $t_c$ (sec). The $O_2$ product contains 92% $O_2$ in the example.

Two key performance variables characterizing any generic oxygen generator are represented by the following equations (1) and (2): (1) Bed Size Factor (BSF)=$7.822 \times 10^{-4}$ $wt_c$/P, lbs (sorbent)/$TPD_c$; and (2) Oxygen Recovery, R=0.92 P/0.2096 F. BSF is critical to define the sorbent inventory of a process. In general, lower BSF is preferred (smaller adsorber beds). Oxygen recovery is a critical variable (higher is better), primarily for PSA & PVSA systems where feed air is compressed before separation. Higher recovery lowers compression duty. However, it is not that critical for a VSA process where only an air blower is used along with a vacuum pump.

For a given process cycle (cyclic process steps, operating conditions, system void, vessel design, individual steps and total cycle times, etc.) and sorbent (sorptive properties), one may define specific $O_2$ productivity of the process as N (=P/w), g·moles/g of sorbent in system/cycle. Hence, equations (3) and (4) apply: (3) BSF=$7.822 \times 10^{-4}$ $t_c$/N; and (4) w=454 BSF×$TPD_c$.

Figure 2:
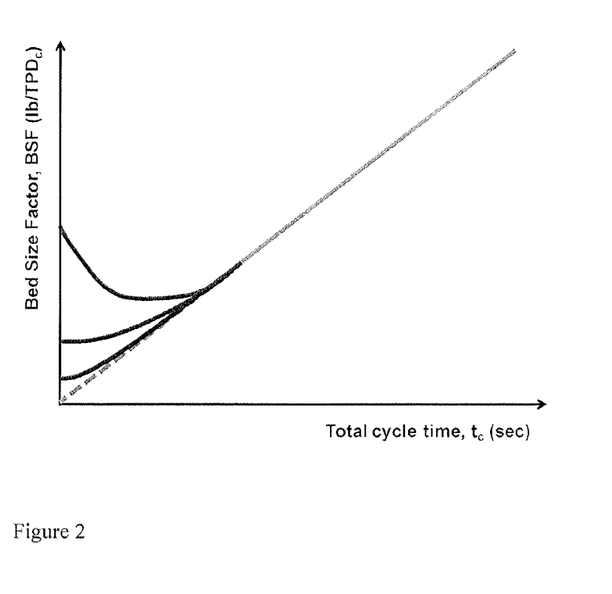
FIG. 2 schematically illustrates adsorbent activity as it relates to bed size factor and total cycle time for a sorptive oxygen concentrator as described herein.

It may be seen from Equations (3) & (4) that for a defined process cycle and sorbent that BSF decreases as $t_c$ decreases provided that N is not, or a weak function of $t_c$. Hence, BSF may linearly decrease with decreasing $t_c$ at larger cycle times, until N becomes a function of $t_c$ due to inefficiency introduced by slower sorption kinetics, gas-solid heat transfer resistance, pressure drop etc, at smaller values of $t_c$ (very fast cycle). Then BSF will not decrease with decreasing $t_c$. It may level off or actually increase. See FIG. 2, for example. Further, for a given $O_2$ productivity ($TPD_c$), the total adsorbent inventory of the process (w) decreases as BSF decreases. In other words, w (or sorber vessel sizes) can be reduced by lowering $t_c$, but only up to a point.

A key goal of the inventors' activities described herein was to demonstrate the existence of the above limitation for a Skarstrom-like PSA cycle using a selected, commercially available adsorbent such as a LiX zeolite. Consequently, in the course of experimentation as described herein, the inventors discovered that the BSF of an adsorptive oxygen generator cannot be indefinitely decreased by lowering the process cycle time beyond a particular cycle time. In other words, the adsorber size cannot be indefinitely reduced below a certain size/amount by simply lowering the cycle time. This phenomenon is novel and was not previously recognized by those skilled in the art. Furthermore, in the preferred embodiments described herein, the inventors intentionally eliminated the requirement of commonly bulky, heavy, and cumbersome vacuum pumps by selecting PSA rather than VSA, PVSA. In that example, the inventors succeeded in showing this lowered BSF compared to various previous studies (as previously cited herein and in FIG. 8) that employed various samples of LiX zeolite and different PSA, VSA and PVSA process schemes (See, e.g. FIG. 8). These combined inventive factors provide for novel compact oxygen concentrators having a greatly reduced bed size and overall apparatus size, weight, and other significant performance characteristics."

The inventors have also discovered apparatus and methods that provide an optimum cycle time for production of ~90% $O_2$ from air, by providing, for example, a PSA cycle using a commercial LiX adsorbent which lowers the design BSF below any previously reported in the literature. In that example, the inventors succeeded in showing this lowered BSF compared to various previous studies (as previously cited herein and in FIG. 6) that employed various samples of LiX zeolite and different PSA, VSA and PVSA process schemes (See, e.g. FIG. 6).

Figure 3:
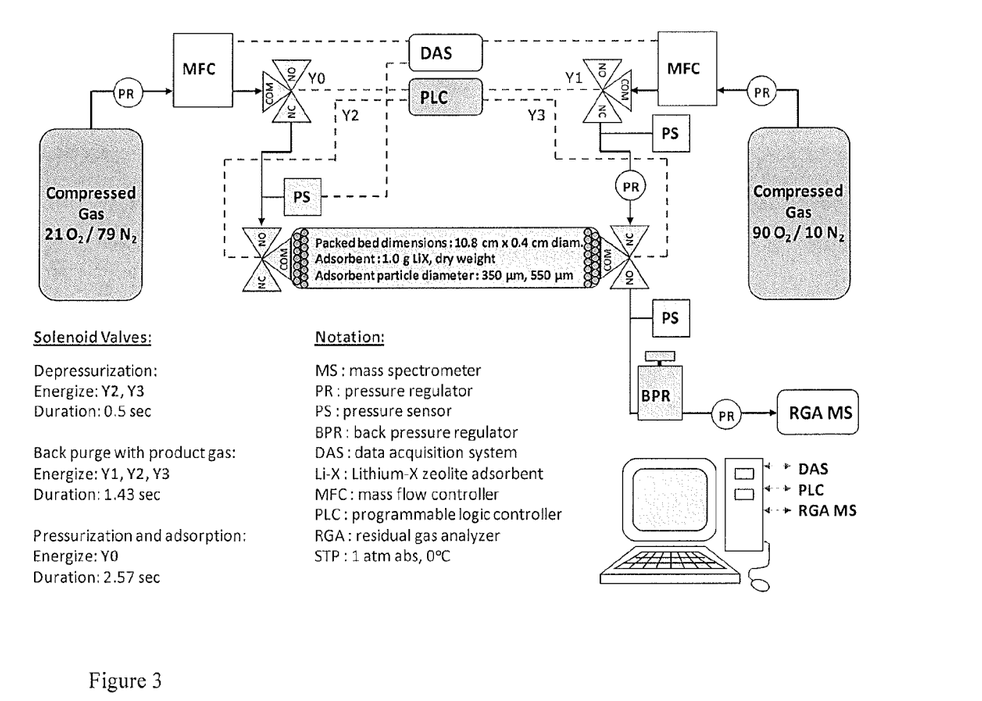
FIG. 3 schematically illustrates a miniature oxygen concentrator in accordance with the present invention.

As further described herein, the inventors have reduced their conceptions to practice by building apparatus that execute inventive method steps. Text and diagrams provided herein are based upon the building, operation, and testing of the apparatus and associated methods. For example, in an exemplary embodiment consistent with FIG. 3, the inventors built a miniature PSA $O_2$ generator. In this embodiment of FIG. 3, the inventors built a miniature oxygen concentrator including a single column of sorbent (about 0.4 cm diameter×10.8 cm long) containing ~1.0 gm of commercial LiX zeolite (~350 micron diameter); having a total volume of about 1.3 cubic cm. Other components of this embodiment are represented in FIG. 3, and discussed further herein. These measurements can be scaled up to meet the oxygen output desired by one skilled in the art.

The PSA cycle used in our tests was very similar to the Skarstrom cycle. The feed gas was dry and $CO_2$ free synthetic air containing no argon. The process steps included:

a. Adsorber pressurization to a super-ambient pressure with compressed feed air at pressure PA
b. Flow of compressed air at PA to produce the ~90% $O_2$ product gas at essentially feed gas pressure
c. Counter-current depressurization to ambient pressure and reject the waste gas
d. Counter-current purge with a synthetic product gas at near ambient pressure and reject the waste gas
e. (Repeat of above cycle beginning from step a., as required)

Figure 4:
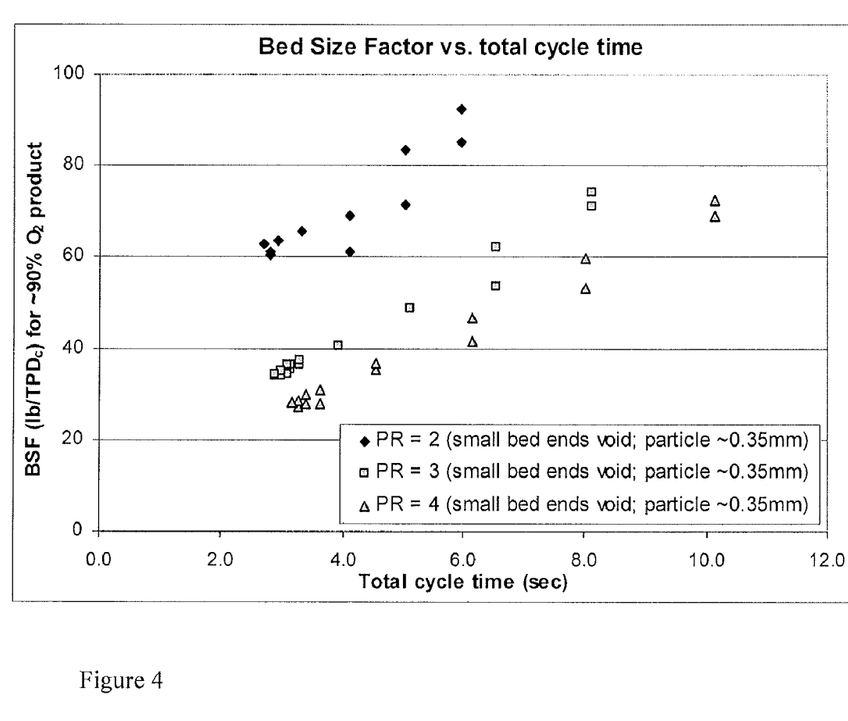
FIG. 4 schematically illustrates results of testing in accordance with the apparatus and methods of the present invention.
Figure 5:
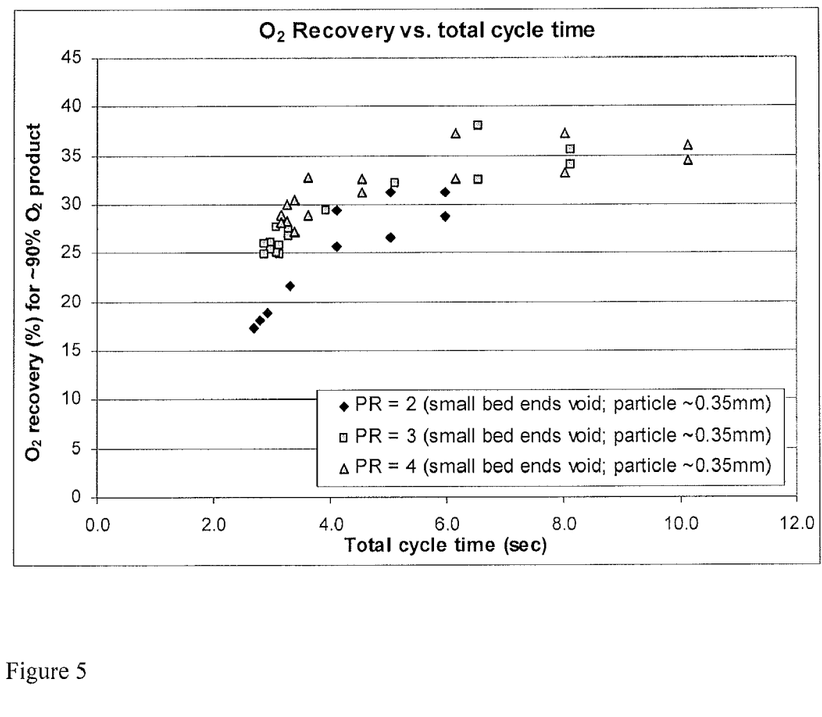
FIG. 5 schematically illustrates results of testing in accordance with the apparatus and methods of the present invention.

Tests were conducted using different adsorption pressures, individual step times and over-all cycle times. The product $O_2$ purity was maintained at ~90% for all runs. Measured variables were BSF and $O_2$ recovery as functions of $t_c$. Only runs where over-all and component mass balances closed within 2% were considered. FIGS. 4 and 5 show the test results (BSF and $O_2$ Recovery as functions of total cycle time) for a system using small particle size of ~350 μm. "PR" indicates pressure ratio of the process (adsorption pressure/desorption pressure), in which desorption was carried out at near ambient pressure while adsorption at 2, 3 and 4 bar.

Figure 6:
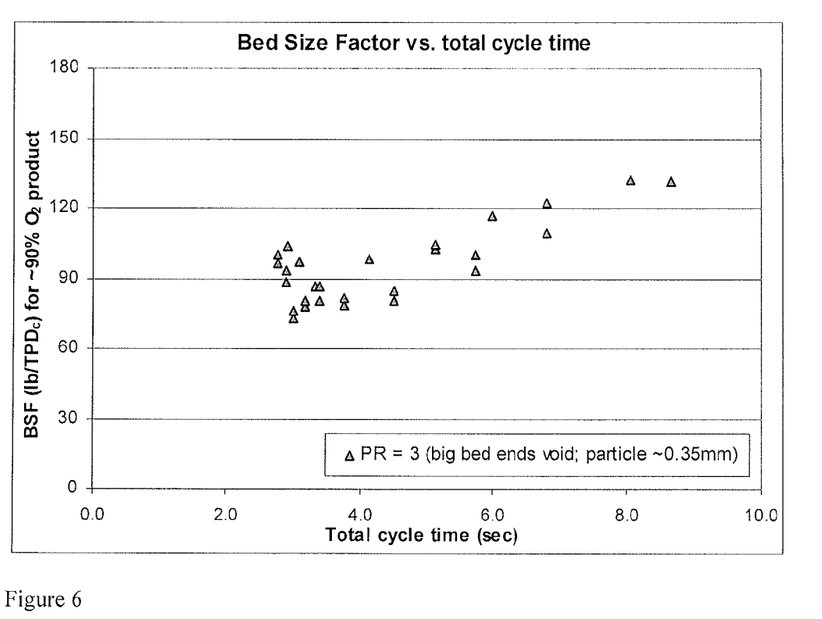
FIG. 6 schematically illustrates results of testing in accordance with the apparatus and methods of the present invention.

In another embodiment, the four step cyclic PSA process described above is combined with and executed using a commercial LiX zeolite provided in a column of approximately the same size as that described in the embodiment of FIG. 3, with a cycle time (tc) of about 2.5 to about 4 seconds, an adsorption pressure of about 3 bar, to produce a Bed Size Factor (BSF) of less than about 50 lb/$TPD_c$. a BSF level not currently reported elsewhere, and clearly distinct from current patented processes, as illustrated in FIG. 6.

FIG. 4 demonstrates that the BSF decreases nearly linearly (as by Equation (3)) as $t_c$ is decreased until $t_c$ reaches ~3.5-4.0 seconds and then it levels off or even increases (at lower adsorption pressures) when the cycle time is further lowered. This demonstrates the basic hypothesis of the inventors that BSF cannot be indefinitely reduced, and hence the adsorbent quantity in the PSA system cannot be reduced indefinitely by simply lowering the cycle time of the PSA process. Furthermore, FIG. 4 shows that the optimum cycle time for lowering BSF is a strong function of feed gas pressure. The adverse effect of lowering cycle time on BSF is more pronounced as the adsorption pressure decreases.

FIG. 5 shows that the $O_2$ recovery decreases as the cycle time is decreased and the adsorption pressure is decreased. This result is expected since void gas quantity in the system at the end of the adsorption step increases as the adsorption pressure increases and a part of the void (air like) is lost as waste gas in each cycle. Faster cycles accentuate this effect.

Figure 7:
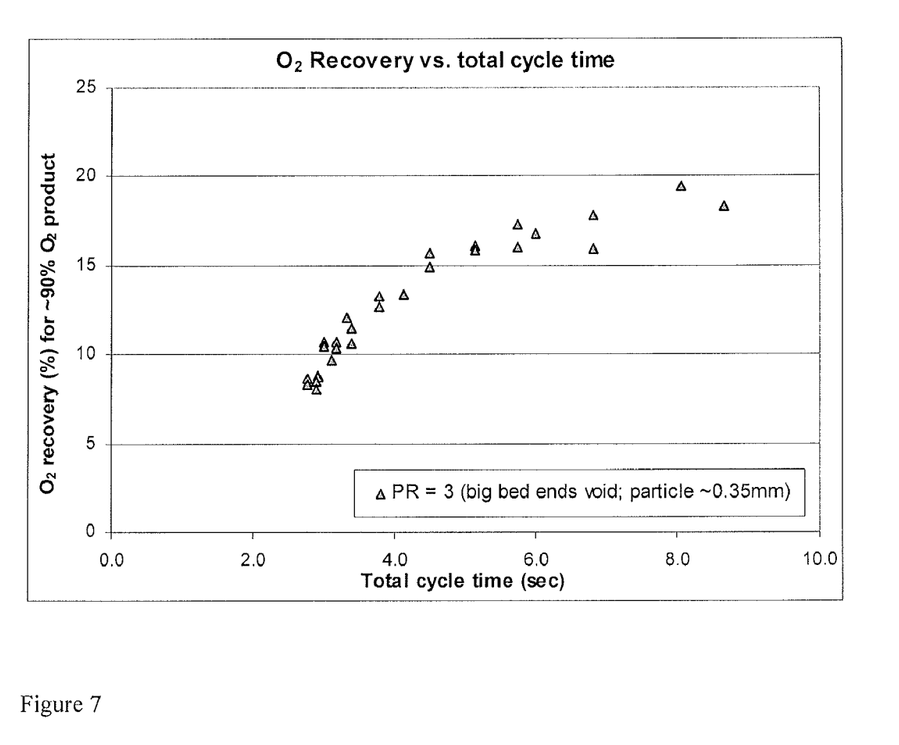
FIG. 7 schematically illustrates results of testing in accordance with the apparatus and methods of the present invention.
Figure 8:
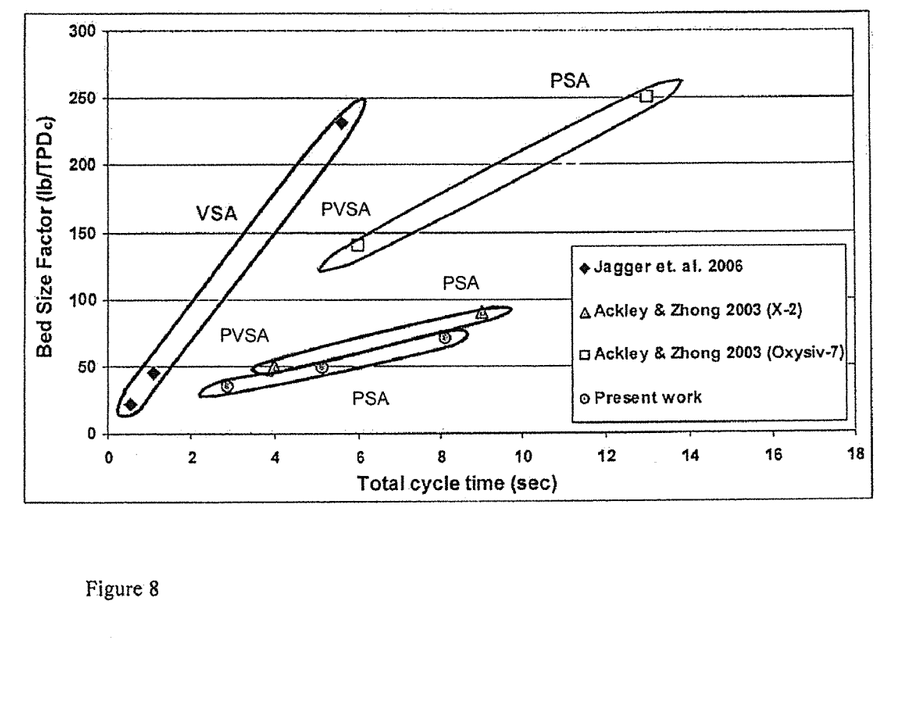
FIG. 8 schematically illustrates results of testing of an embodiment of the present invention compared to embodiments of existing oxygen concentrator apparatus and methods as described in the cited literature.

FIGS. 6 and 7 show the test results (BSF and $O_2$ Recovery as functions of total cycle time) for a system including a column of the same size as that described for FIG. 3, but having a bigger void volume than that of the apparatus used to generate the date of FIGS. 4-5 at the bed ends and using small particle size of ~350 μm. FIG. 6 shows that the experimentally measured BSF decreases nearly linearly (as by Eqn. 3) as $t_c$ is decreased until $t_c$ reaches ~3.5-4.0 seconds and then it levels off and even increases when the cycle time is further lowered, as shown schematically in FIG. 2. These figures illustrate the basic hypothesis of the inventors that BSF cannot be reduced indefinitely, and hence the adsorbent quantity in the PSA system can not be reduced indefinitely, by simply lowering the cycle time of the PSA process. Furthermore, FIG. 4 shows that the optimum cycle time for lowering BSF is a strong function of feed gas pressure. The adverse effect of lowering cycle time on BSF is more pronounced as the adsorption pressure decreases FIG. 7 shows that the $O_2$ recovery decreases as the cycle time is decreased and the adsorption pressure is decreased. With bigger void volume at the bed ends, $O_2$ recovery drops significantly as compared to those in FIG. 5 those FIG. 8 compares the BSF measured by the inventors' testing as functions of cycle times for pressure ratio of 3 and $O_2$ purity of ~90%. Also shown are published data which were obtained using various PSA, VSA and PVSA cycles, but all employing some variety of LiX zeolite. FIG. 8, shows that (a) the present inventive PSA system and methods are capable of producing a BSF of less than 50 when a cycle time of 3-4 seconds and a adsorption pressure at 3 bar is used. This magnitude of BSF could not be achieved by published PSA or PVSA data. Only a very rapid VSA system operating at a very small cycle time of less than 2 seconds could break that barrier. However a very rapid VSA process would require a very large vacuum pump and special valves like rotating valves. Thus such a VSA process may be difficult to design and operate. In contrast, the inventive PSA apparatus and methods do not require use of a vacuum pump.

Consequently, the inventors have discovered oxygen concentrator methods and apparatus that rely on a simple PSA process that is surprisingly efficient, and that provides significant size reduction and advantage as compared to known concentrators. In a preferred embodiment, the inventive apparatus and methods utilize a novel four-step process consisting of four steps: 1) Feed air pressurization to a super-ambient pressure; 2) Air adsorption to produce ~90% $O_2$ product at feed pressure; 3) Counter-current depressurization to ambient pressure, and 4) Countercurrent product purge. In an example wherein LiX zeolite is provided as the adsorbent, the apparatus and methods can produce a BSF of less than 50 when operated with a total cycle time of 2.5-4 seconds and an adsorption pressure of 3 bar. Such performance criteria are unmatched by any known compact or portable oxygen concentrators.

ADDITIONAL EXAMPLES

Figure 9:
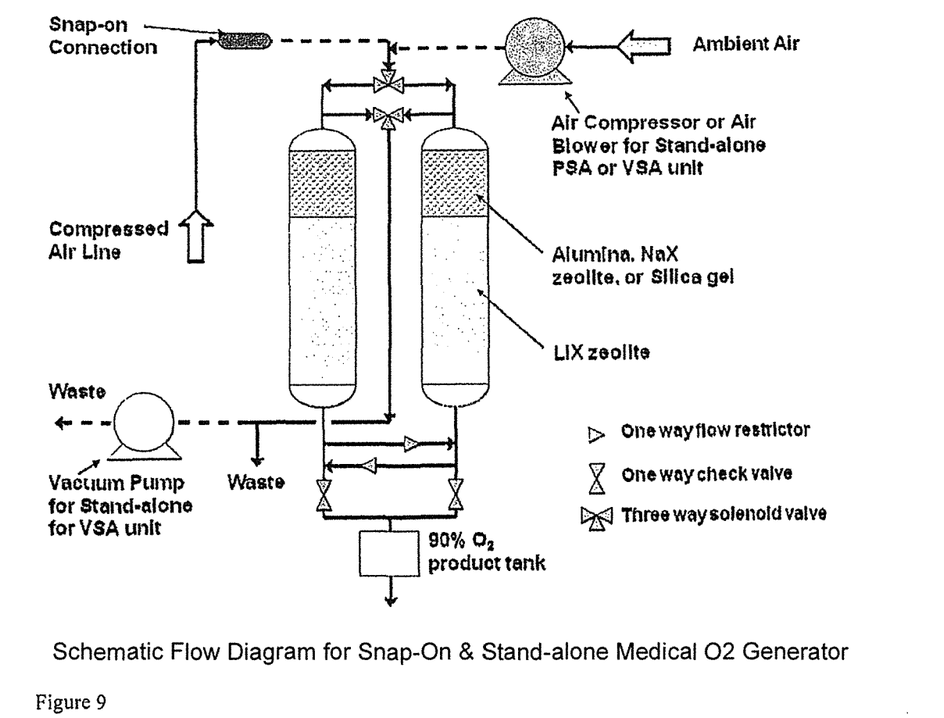
FIG. 9 schematically illustrates an embodiment of the apparatus and methods in accordance with the present invention.

The small and light-weight adsorptive oxygen concentrator systems and methods described herein can be applied in many ways. In one inventive application, the inventors have utilized the methods and apparatus to provide for a snap-on type concentrator For example, a compact oxygen concentrator having a rapid PSA cycle ("rapid" as used herein means less than about 10 seconds total cycle time) can be utilized by installing (or "snapping on") into any existing compressed air stream line already provided and available (e.g. civil, military, hospital, tanks, airlines, ships, submarines, undersea, caves and mines, etc.). This is illustrated in FIG. 9. No known oxygen concentrator provides this snap-on feature, which provides the unprecedented advantage of providing oxygen of greater than about 90% purity from a miniature oxygen concentrator and without the need for an air compressor.

In another embodiment, also shown in FIG. 9, a compact stand-alone concentrator can be provided using a rapid PSA or VSA cycle in situations where a compressed air stream is not already available (e.g. home). In embodiments where VSA is desired, a vacuum pump is included. However, as illustrated, in "snap on" embodiments and other concentrator embodiments where only the inventive PSA is desired, no vacuum pump is required.

Described below is an example of process steps and times for each bed of the process and apparatus described in an inventive "snap-on" or "stand-alone" oxygen concentrator such as, for example, the embodiment of FIG. 7 hereof. Two beds in parallel ensure continuous production. In this example, the process involves the steps of: 1) Simultaneous pressurization (if needed), followed by; 2) adsorption to produce ~90% $O_2$ product at feed air pressure [3-4 bars for PSA, 1.1-1.4 bars for VSA in a total cycle time of about 3-5 seconds. Next, the process involves 3) Simultaneous counter-current depressurization [3-4 bars to ~1 bar for PSA] or evacuation [1.1-1.4 bar to ~0.15 bar for VSA] with product $O_2$ back purge, followed by; 4) product pressurization from lowest desorption pressure to about feed air pressure, in a cycle time of about 3-5 seconds.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A rapid cyclic pressure swing adsorption (PSA) method for producing an oxygen enriched gaseous product containing more than 85 mole % oxygen, the method comprising the steps of:
   a) providing a feed gas comprising compressed ambient air;
   b) providing a gas separation apparatus comprising at least one adsorber column, the adsorber column packed with at least a layer of a desiccant adsorbent comprising particles of more than 1.0 mm hydraulic diameter in the feed gas side and at least a layer of a nitrogen selective particles of less than 0.5 mm hydraulic diameter in the product gas side; and
   c) carrying out a PSA separation process, the process comprising the steps of:
      (1) co-currently pressurizing the at least one adsorber column using the received compressed ambient air;
      (2) co-currently directing flow of the compressed ambient air to produce an oxygen enriched product gas at a near feed gas pressure;
      (3) performing counter-current depressurization of the at least one adsorbent column to a near ambient pressure; and
      (4) performing a counter-current oxygen purge at ambient or sub-ambient pressure using at least a portion of the oxygen enriched product gas.

2. The method of claim 1, wherein the total PSA separation process cycle time is between about 1 to about 10 seconds, and wherein the bed size factor is below about 70.

3. The method of claim 1, wherein the method does not include any use of vacuum assist.

4. The method of claim 2, wherein the adsorbent column comprises a layer of a nitrogen selective LiX zeolite in the product gas side.

5. The method of claim 1, wherein the feed gas pressure is above about 2 bar.

6. The method of claim 1, wherein the feed gas pressure is between about 3 to about 4 bars.

7. The method of claim 1 where the feed air temperature is near ambient.

8. The method of claim 1 where the desiccant adsorbent is alumina, silica gel, or NaX zeolite.

9. The method of claim 1 where the average nitrogen selective particle diameter is about 0.35 mm and the average desiccant particle diameter is about 2 mm.

10. The method of claim 1 where the feed air pressure is about 3 to 4 bars, the total cycle time is between 2 to 6 seconds, the product oxygen purity is at least 90 mole percent (%), and the BSF is less than 50.

11. The process in claim 1 where the steps (1) and (2) are carried out at a super atmospheric pressure and step (4) is carried out at a sub atmospheric pressure.

12. The method of claim 11 where the super atmospheric pressure is less than 2 bar and the sub atmospheric pressure is greater than 150 torr.

13. The method of claim 1 where an external air compressor is used to supply the feed gas as compressed air to the PSA system.

14. The method of claim 1 wherein the apparatus has adsorbent volume such that the BSF is less than 70.

15. The method of claim 1, wherein the apparatus includes fixtures for installation into the compressed air outlet of an existing external air compressor.

16. An apparatus for executing rapid cyclic pressure swing adsorption (PSA) methods for producing an oxygen enriched gaseous product containing more than 85 mole % oxygen, the apparatus comprising:
   a) a gas separation apparatus comprising at least one adsorber column, the adsorber column packed with at least a layer of a desiccant adsorbent comprising particles of more than 1.0 mm hydraulic diameter in the feed gas side and at least a layer of a nitrogen selective particles of less than 0.5 mm hydraulic diameter in the product gas side; and b) means for carrying out a PSA separation process, the process comprising the steps of:
  (1) co-currently pressurizing the at least one adsorber column using the received compressed ambient air;
  (2) co-currently directing flow of the compressed ambient air to produce an oxygen enriched product gas at a near feed gas pressure;
  (3) performing counter-current depressurization of the at least one adsorbent column to a near ambient pressure; and
  (4) performing a counter-current oxygen purge at ambient or sub-ambient pressure using at least a portion of the oxygen enriched product gas.

17. The apparatus of claim 16, wherein the total PSA separation process cycle time is between about 1 to about 10 seconds, and wherein the bed size factor is below about 70.

18. The apparatus of claim 16, wherein the apparatus does not include any use of vacuum assist.

19. The apparatus of claim 16, where the feed air pressure is about 3 to 4 bars, the total cycle time is between 2 to 6 seconds, the product oxygen purity is at least 90 mole percent (%), and the BSF is less than 50.

* * * * *